United States Patent
Buttin et al.

(10) Patent No.: US 12,089,857 B2
(45) Date of Patent: Sep. 17, 2024

(54) SYSTEM FOR SURGICAL TREATMENT OF THE SPINE

(71) Applicant: SYLORUS ROBOTICS, Saint-Priest (FR)

(72) Inventors: Romain Buttin, Saint Priest (FR); Gautier Daune, Bron (FR); Pierre Roussouly, Saint Cyr Au Mont D'Or (FR)

(73) Assignee: SYLORUS ROBOTICS, Saint-Priest (FR)

( * ) Notice: Subject to any disclaimer, the term of this patent is extended or adjusted under 35 U.S.C. 154(b) by 430 days.

(21) Appl. No.: 17/430,108

(22) PCT Filed: Feb. 13, 2020

(86) PCT No.: PCT/EP2020/053728
§ 371 (c)(1),
(2) Date: Aug. 11, 2021

(87) PCT Pub. No.: WO2020/165327
PCT Pub. Date: Aug. 20, 2020

(65) Prior Publication Data
US 2022/0142680 A1 May 12, 2022

(30) Foreign Application Priority Data
Feb. 14, 2019 (FR) ....... 1901513

(51) Int. Cl.
*A61B 17/70* (2006.01)
*A61B 17/16* (2006.01)
(Continued)

(52) U.S. Cl.
CPC ...... *A61B 17/1671* (2013.01); *A61B 17/7032* (2013.01); *A61B 17/7082* (2013.01);
(Continued)

(58) Field of Classification Search
CPC .............. A61B 17/7082; A61B 17/1671
See application file for complete search history.

(56) References Cited

U.S. PATENT DOCUMENTS 3,346,894 A 10/1967 Lemelson
5,573,537 A * 11/1996 Rogozinski ........ A61B 17/7092
606/80

(Continued)

FOREIGN PATENT DOCUMENTS

EP 1937160 A2 7/2008
EP 2849652 A1 3/2015
(Continued)

OTHER PUBLICATIONS

Search Report for International Patent Application No. PCT/EP2020/053728 dated Jun. 2, 2020.
(Continued)

*Primary Examiner* — Christian A Sevilla
(74) *Attorney, Agent, or Firm* — Pearne & Gordon LLP

(57) ABSTRACT

A surgical treatment system comprises a drill bit extending along a proximo-distal drill bit axis suitable for drilling a hole in the pedicle of a vertebra when the bit is rotated. The bit includes, successively along the drill bit axis, a distal end, a cylindrical drill centred on the drill bit axis for drilling the hole by cutting into and removing bone material from the pedicle to give a distal end portion of the hole a cylindrical shape, and a milling cutter for cutting bone material from the pedicle of the vertebra to give a proximal end portion of the hole a funnel shape gradually widening from the distal end portion of the hole. A pedicle screw extends along a proximo-distal screw axis and is designed to be screwed into the hole by being rotated after the drill bit has drilled the hole and has been removed from this hole.

18 Claims, 4 Drawing Sheets

(51) Int. Cl.
  *A61B 17/86* (2006.01)
  *A61B 17/00* (2006.01)
  *A61B 90/00* (2016.01)

(52) U.S. Cl.
  CPC  *A61B 17/8625* (2013.01); *A61B 2017/00212* (2013.01); *A61B 2017/00398* (2013.01); *A61B 2090/064* (2016.02)

(56) References Cited

U.S. PATENT DOCUMENTS

| | | | |
|---|---|---|---|
| 6,443,956 B1 * | 9/2002 | Ray | A61B 17/1671 606/80 |
| 2003/0109883 A1 * | 6/2003 | Matsuzaki | A61B 17/1671 606/86 R |
| 2005/0209622 A1 * | 9/2005 | Carrison | A61B 17/1671 606/170 |
| 2005/0240201 A1 * | 10/2005 | Yeung | A61B 17/1604 606/108 |
| 2008/0262526 A1 | 10/2008 | Neubardt et al. | |
| 2013/0331840 A1 * | 12/2013 | Teisen | A61B 17/1615 606/80 |
| 2018/0199951 A1 | 7/2018 | Chappuis et al. | |

FOREIGN PATENT DOCUMENTS

| | | |
|---|---|---|
| WO | 2012068641 A1 | 5/2012 |
| WO | 2016019035 A1 | 2/2016 |

OTHER PUBLICATIONS

Search Report for French Application No. FR 1901513 dated Dec. 6, 2019.

\* cited by examiner

SYSTEM FOR SURGICAL TREATMENT OF THE SPINE

The present invention relates to a system for surgical treatment of the spine. It also relates to a method for drilling a patient's vertebra, and a method for screwing into a patient's vertebra.

The surgical treatment of the spine of human patients can lead to the placement of spinal implants. For example, in order to perform arthrodesis of a segment of several vertebrae, implants are attached to the vertebrae in order to set them together. These implants often include so-called pedicle screws, which are placed in the pedicles of the vertebrae. The surgical procedures required to place these pedicle screws are difficult to perform due to the small size of the bone structures where the screws are placed, the lack of visibility and the criticality of the surrounding anatomical structures, such as the spinal cord, the vena cava, the aorta, etc. In addition, if the pedicle screws are incorrectly positioned, the spinal implant may break or loosen.

In practice, these surgical procedures are currently performed by orthopedic and neuro-orthopedic surgeons who, after having cleared a posterior access to the vertebrae, use ad hoc tools on the latter, in particular bone drilling and screwing tools. To guide their actions, surgeons can work "freehand" using either anatomical benchmarks, or radiographic sights provided by a block imager such as an image intensifier, or an intraoperative computer navigation system. Surgeons can also be assisted by surgical robots that position a guide in relation to the patient's spine to be operated on, into which or on which the surgeon introduces or places a tool that the surgeon manipulates when applying this tool to the spine: this positioning guide is a drilling guide, for example, which is precisely positioned by the robot according to intraoperative data and which is provided with a hole into which the surgeon introduces a drilling tool, it being noted that it is not the robot itself that applies the drilling tool, as proposed in US 2018/199951.

These various operative techniques minimize the risk of perforating through the vertebra and thus damaging surrounding anatomical structures, in particular vital structures such as the spinal cord, the vena cava, the aorta, etc. However, their result remains dependent, at least in part, on the surgeon's movement and thus on the surgeon's expertise and skill level. Furthermore, the final positioning of the pedicle screw in relation to the vertebra is not completely controlled, as it has been observed that the direction of progression of the screw in the vertebra during screwing may deviate slightly from the desired placement trajectory.

U.S. Pat. No. 5,573,537 proposed a special surgical drill for the spine. This drill bit comprises successively a distal end portion, an intermediate portion and a proximal end portion. The distal end portion, referred to as a probing element in U.S. Pat. No. 5,573,537, may have a generally cylindrical shape, flanked by two opposing bevels: this distal end portion is not suitable for piercing the cortical bone of a vertebra, but is intended to be inserted into the opening after an opening has been made through the cortical bone of the vertebra and then to penetrate the cancellous bone of the pedicle of the vertebra, forming a pilot hole. The intermediate part of the drill bit is also generally cylindrical and is provided with cutting elements that, when the drill bit is rotated on itself, allow a rear anchoring hole to be made in the pedicle. This rear anchoring hole is cylindrical, so that this rear anchoring hole and the aforementioned front hole together form a stepped hole. The proximal end portion has a smooth cylindrical shape, which extends the intermediate portion and which has a truncated conical flare opposite the latter, forming a leg collar for mechanically connecting the drill bit to a rotating drive tool: the smooth outer surface of this proximal end portion is provided with circumferential lines constituting penetration indications. When drilling the rear anchor hole, the distal end portion of the drill bit provides some guidance for the drill bit by interacting with the sponge material at the pilot hole. However, the stepped shape of the resulting final hole does not improve subsequent placement of a pedicle screw.

EP 1937160 proposed a spinal drill bit that is functionally similar to that of U.S. Pat. No. 5,573,537.

The purpose of the present invention is to provide a system for surgical treatment of the spine, which improves the placement of pedicle screws in vertebrae.

To this end, the subject matter of the invention is a spinal surgical treatment system, comprising:
- a drill bit, that extends along a proximo-distal drill axis and that is suitable for drilling a hole in the pedicle of a vertebra of a patient when the drill bit is rotated on itself about the drill axis, this drill bit including, successively, along the drill axis:
  - a distal end,
  - a cylindrical drill, centered on the drill axis and suitable for drilling the hole by cutting into and removing bone material from the pedicle of the vertebra so as to give a distal end portion of the hole a cylinder shape, and
  - a milling cutter designed to cut the bone material from the pedicle of the vertebra so as to give a proximal end portion of the hole a funnel shape gradually widening from the distal end portion of the hole, and
- a pedicle screw that extends along a proximo-distal screw axis and that is designed to be screwed into the hole, by being rotated on itself about the screw axis, after the drill bit has drilled the hole in the pedicle of the vertebra and has been removed from this hole, wherein the pedicle screw includes a threaded rod, which comprises a distal end constituting a distal end of the pedicle screw, and which has a cylindrical shape, which is centered on the screw axis and whose nominal diameter is greater than a diameter of the drill.

One of the ideas behind the invention is to prepare the placement trajectory of a pedicle screw by making a hole in the pedicle of the vertebra prior to application of this screw to a patient's vertebra, this hole being drilled by a specific drill that gives the proximal end portion of the hole a funnel shape: in this way, when the pedicle screw is presented at the entrance of this hole, the distal end of the pedicle screw can interact by contact with the funnel so as to center the pedicle screw in the hole and thus align it with the axis of the hole, this axis having been precisely positioned on the vertebra by the drill bit when drilling the hole. Thus, when the pedicle screw is applied to the vertebra in a manner that is offset from the trajectory that the drill had followed to drill the hole, the pedicle screw is naturally brought back into the axis of the hole. The funnel shape results from the presence of a milling cutter, a conical one for example, which is provided at the proximal end of a cylindrical drill, connecting the milling cutter to the distal end of the drill bit. This drill, which gives a cylindrical shape to the distal end portion of the hole, has a diameter smaller than the nominal diameter of the threaded rod of the pedicle screw, so that this threaded rod is guided coaxially into the distal end portion of the hole during screwing. Thanks to the invention, the placement of the pedicle screw is thus particularly precise.

Moreover, this placement can advantageously be checked intraoperatively before screwing in the pedicle screw, by using an ad hoc device, such as a metal probe, which is introduced into the hole and which allows the surgeon to easily check the position of the hole within the vertebra, for example by direct palpation of this device or by intraoperative radiography.

The system according to the invention can be used manually by the surgeon, i.e., the drill bit and the pedicle screw are then rotated by ad hoc motorized devices, handheld by the surgeon. This said, the invention finds a particularly advantageous application in the case where the motorized devices for driving the drill bit and the pedicle screw are "held" by a surgical robot, i.e. moved specially by this robot, with it emphasized that the robot itself performs the surgical act of drilling and screwing into the vertebrae, and this with precision and repeatability. In this case, in order to further improve the performance of the corresponding surgical treatment system, by avoiding any deviation in the placement in the vertebrae with respect to the positioning requested from the robot by the surgeon, the system can advantageously be provided to adjust the movement of the devices motorized by the robot and thus control the drill bit position when drilling the hole and control the pedicle screw position when screwing into the hole, taking into account the forces exerted on the patient's vertebra by the drill bit when drilling and by the pedicle screw when screwing, as explained in more detail later.

According to additional advantageous features of the surgical treatment system according to the invention:
- the milling cutter has a conical shape that is centered on the drill axis and diverges proximally from the drill;
- the distal end of the drill bit is pointed and centered on the drill axis;
- diameter of the drill bit is substantially equal to the diameter of the threaded rod, measured at the base of the thread of the threaded rod;
- the distal end of the threaded rod has a substantially conical shape, which is centered on the screw axis and diverges in the proximal direction;
- the system further comprises an intraoperative control member, which is adapted to be introduced into the hole, after the drill bit has drilled the hole in the pedicle of the vertebra and has been removed from this hole and before the pedicle screw is screwed into the hole, so as to control the positioning of the hole in the vertebra, in particular by palpation and/or radiography;
- the system further comprises:
  a motorized device adapted to rotate the drill bit about the drill axis and/or to rotate the pedicle screw about the screw axis, and
  a robot adapted to spatially move the motorized device;
- the motorized device is equipped with a force sensor configured to measure at least one component of the forces exerted on the vertebra by the drill bit when drilling the hole and/or by the pedicle screw when screwing into the hole, and wherein the system further comprises an electronic unit adapted to control the movement of the motorized device by the robot as a function of said at least one component measured by the force sensor;
- the electronic unit is configured both to analyze said at least one component measured by the force sensor, in particular by comparing said at least one component to a predetermined value or by time tracking said at least one component, and to control the movement of the motorized device by the robot from the result of the analysis of said at least one component; and
- the electronic unit is configured to control the movement of the motorized device by the robot so as to keep substantially constant the at least one component measured by the force sensor.

It will be noted that the technical considerations for movement control by the robot, based on measurement of the forces exerted during drilling or screwing, can be implemented independently of the specifics of the drill bit and the pedicle screw.

Moreover, it is also an object of the invention to provide a method for drilling a vertebra of a patient, wherein:
- a drill bit is both rotated about its axis and moved spatially by a robot, so as to drill a hole in a pedicle of the vertebra,
- at least one component of the forces exerted by the drill bit on the vertebra is measured during drilling the hole, and
- the movement of the drill bit by the robot is controlled as a function of said at least one component.

According to additional advantageous features of this drilling method:
- the movement of the drill bit by the robot is controlled based on an analysis of said at least one component, including by comparing said at least one component to a predetermined value or by time tracking said at least one component.
- the movement of the drill bit by the robot is controlled to keep the at least one component substantially constant.
- said at least one component is measured by a force sensor integrated with a motorized device that is adapted to rotate the drill bit about its axis and to be moved spatially by the robot.

It is also an object of the invention to provide a method for screwing into a vertebra of a patient, wherein:
- a pedicle screw is both rotated about its axis and moved spatially by a robot, so as to screw the pedicle screw into a pedicle of the vertebra,
- at least one component of the forces exerted by the pedicle screw on the vertebra is measured during screwing the pedicle screw, and
- the movement of the pedicle screw by the robot is controlled as a function of said at least one component.

According to additional advantageous features of this screwing method:
- the movement of the pedicle screw by the robot is controlled based on an analysis of the at least one component, including by comparing the at least one component to a predetermined value or by time tracking the at least one component.
- the movement of the pedicle screw by the robot is controlled to keep the at least one component substantially constant.
- the at least one component is measured by a force sensor integrated with a motorized device that is adapted to rotate the pedicle screw about its axis and to be moved spatially by the robot.

The invention will be better understood from the following description, given only by way of example and made with reference to the drawings in which.

FIG. 3 and

Figure 1:
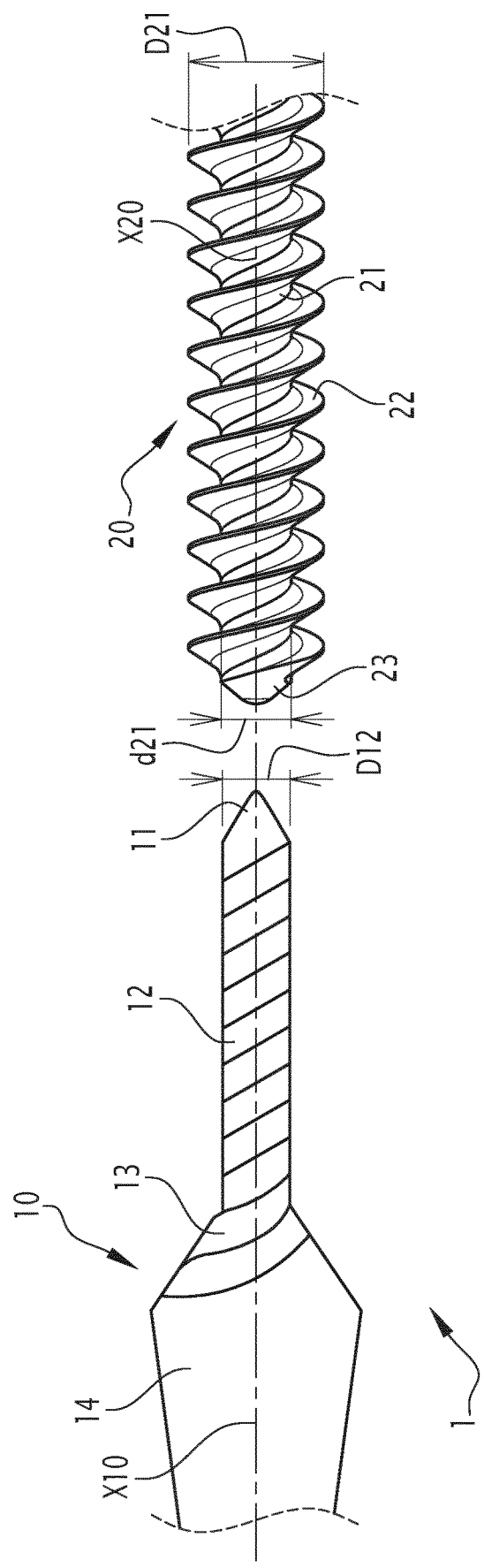
FIG. 1 is an elevated view of a drill bit and a pedicle screw belonging to a surgical treatment system according to the invention.
Figure 2:
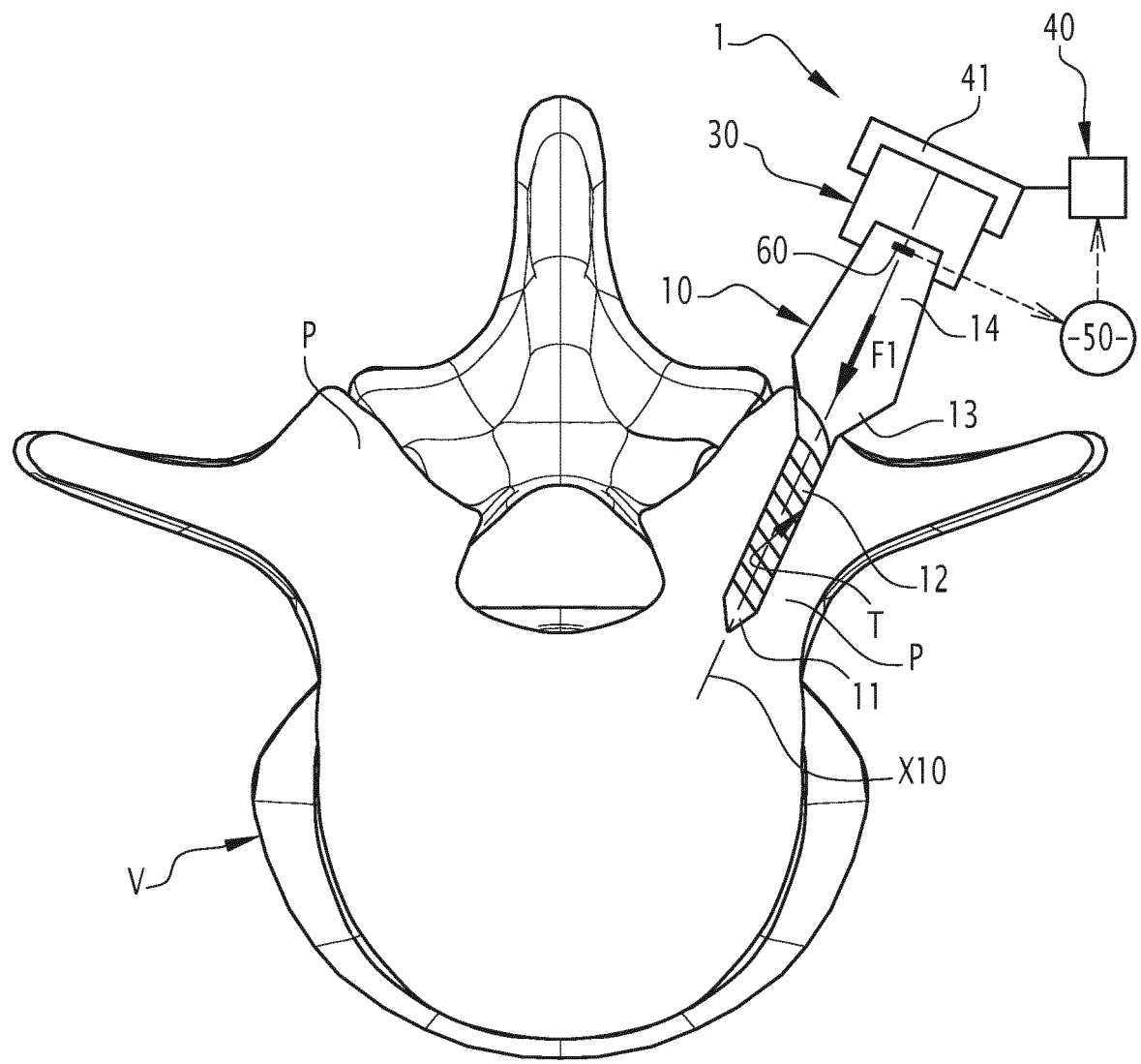
FIG. 2 is a schematic of the drill bit of FIG. 1, together with other elements of the treatment system according to the invention and shown in use on a human vertebra, viewed in cross section.
Figure 4:
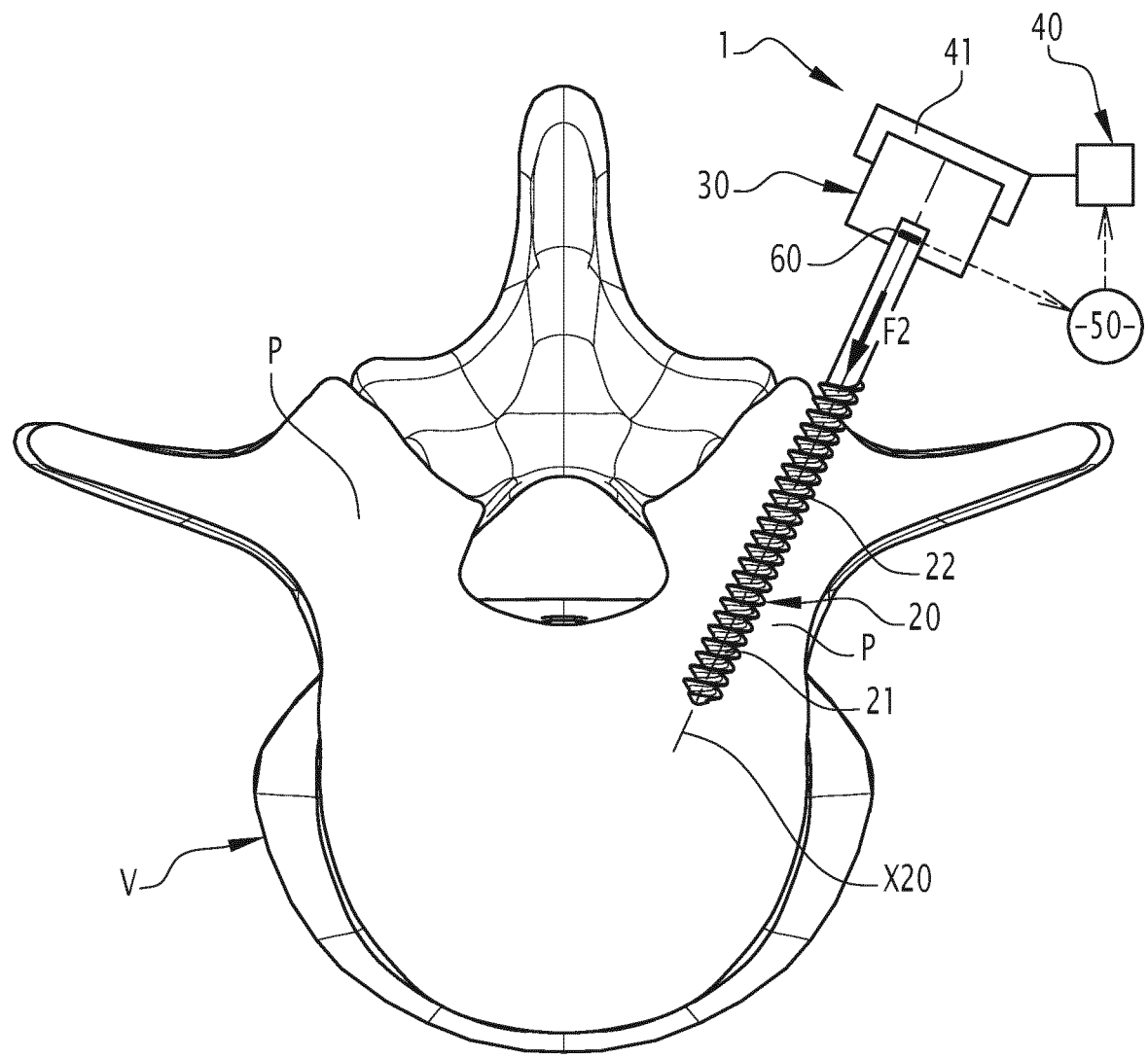

FIG. 4 are views similar to FIG. 2, illustrating the application of the pedicle screw of FIG. 1 to the vertebra by the surgical treatment system.

FIGS. 1 through 4 depict a system 1 for performing surgical treatment of the human spine.

This system 1 comprises a drill bit 10 and a pedicle screw 20, shown alone in FIG. 1.

The drill bit 10 has a generally elongated shape and defines a proximo-distal drill axis X10, along and around which the drill bit 10 extends in length. The drill bit 10 includes, in sequence along the drill axis X10, a distal end 11, a drill 12, a milling cutter 13, and a proximal end shank 14.

The drill 12 has a cylindrical shape, centered on the drill axis X10. When the drill bit 10 is rotated about the drill axis X10, the drill 12 is able to drill a cylindrical hole in a bone material, the diameter of the cylindrical hole obtained corresponding substantially to the diameter D12 of the drill 12. For this purpose, the drill 12 is, for example, provided with helical grooves with a cutting edge, which wind around the drill axis X10 along the drill 12. The specific features of the drill 12, which allow the bone material to be notched and evacuated in order to make the aforementioned cylindrical hole, are not limiting to the invention.

As for the milling cutter 13, it has a shape that progressively widens in the proximal direction from the drill 12, relative to the drill axis X10. Thus, the milling cutter 13 has a minimum diameter at its distal end of junction with the drill 12 corresponding to the diameter D12 of the drill, while the milling cutter 13 has a maximum diameter, at its proximal end of junction with the proximal end shank 14, greater than the aforementioned minimum diameter. Between its distal and proximal ends, the cutter 13 has an increasing, in particular continuously increasing, diameter along the drill axis X10. According to a practical embodiment that is implemented in the example considered in the Figures, the milling cutter 13 thus has a conical shape, which is centered on the drill axis X10 and diverges in the proximal direction from the drill 12. Regardless of the geometric specifics of the milling cutter 13, when the drill bit 10 is rotated on itself about the drill axis X10, this milling cutter makes it possible to produce a funnel-shaped cavity in a bone material that gradually flares out in a proximal direction from the distal end of this cavity. For this purpose, the milling cutter 13 is provided with external reliefs with a cutting edge for example, which mechanically cut into the bone material to produce the funnel-shaped cavity therein: the structural features of the milling cutter 13, allowing the bone material to be cut into the funnel-shaped cavity, are not limiting to the invention.

To enable the drill bit 10 to be driven into a bone material to be drilled, the distal end 11 advantageously has a pointed, typically conical shape centered on the drill axis X10.

The pedicle screw 20, which is intended to be placed in the pedicle of a human vertebra, defines a proximo-distal screw axis X20, along and around which the pedicle screw 20 extends in length. The pedicle screw 20 includes a threaded rod 21 at the distal part and a head at the proximal part: in FIG. 1, only the threaded rod 21 is shown, it being noted that the head of the pedicle screw 20 is not limiting of the invention provided this head is capable of being mechanically engaged to rotate the pedicle screw 20 about the screw axis X20, in a manner known per se.

The threaded rod 21 has a cylindrical shape, which is centered on the screw axis X20 and whose nominal diameter D21 is defined in a usual manner by the external edge of a thread 22 winding around the screw axis X20 along the threaded rod 21. This nominal diameter D21 is greater than the diameter D12 of the drill 12, as clearly visible in FIG. 1. According to a preferred embodiment illustrated in the Figures, the diameter D12 of the drill 12 is substantially equal to the diameter D21 of the threaded rod 21, measured at the base of the thread 22.

The threaded rod 21 includes a distal end 23 that constitutes the distal end of the pedicle screw 20, as shown in FIG. 1. In an embodiment that is advantageous for reasons that will become apparent later, this distal end 23 has a substantially conical shape, which is centered on the screw axis X20 and diverges in the proximal direction.

The surgical treatment system 1 includes other elements that will be discussed below in the context of describing the use of the drill 10 and the pedicle screw 20 successively applied to a vertebra V of a patient's spine, with reference to FIGS. 2 through 4.

The use of the drill bit 10 and the pedicle screw 20 is implemented in the context of a surgical procedure, during which the vertebra V is first accessed from the posterior.

Then, the drill bit 10 is used in a drilling step in which the drill bit 10 drills a hole T in one of the pedicles P of the vertebra V. To do this, the drill bit 10 is first moved into the space, to be brought closer to the vertebra, until it is applied to the vertebra so as to plant the distal end 11 of the drill bit 10 in the vertebra, the pointed shape of the distal end 11 allowing for a clean, non-slip application of the drill bit to the vertebra. The drill bit 10 is then rotated around the drill axis X10, while being moved spatially so as to progress in the pedicle P of the vertebra V, this progression of the drill bit 10 being carried out along a direction of movement indicated by an arrow F1 in FIG. 2 and which extends parallel to the drill axis X10. Due to its rotation and movement, the drill bit 10 pierces the pedicle P progressively until the milling cutter 13 reaches and progresses into the vertebra V, it being noted that the proximal end 14 always remains outside the vertebra V. The hole T thus drilled by the drill 10, more visible in FIG. 3, includes a distal end portion T1, having a cylindrical shape given to it by the drill 12, and a proximal end portion T2, having a funnel shape progressively widening out from the distal end portion T1, the milling cutter 13 having given it this funnel shape at the end the drill bit 10.

In practice, the diameter D12 of the drill 12 is small enough to minimize the risk of damaging the side walls of the pedicle P during the drilling step, the pedicle being similar to a bone tube having a variable diameter of 5 to 12 mm. In addition, the drill 12 is designed to be relatively short, in the sense that, at the end of the drilling step, the distal end 11 of the drill bit 10 reaches the vertebral body of the vertebra V, but is not deeply embedded in it. In this way, at the end of the drilling step, the drill bit 10 reaches the vertebral body of the vertebra V, without taking the risk of going beyond the anterior bony limits of the vertebra, which protect noble anatomical, in particular vascular structures, in front of the vertebra.

In order to rotate the drill bit 10 during the drilling step, the surgical treatment system 1 includes a motorized device 30. The specifics of this motorized device 30 for the purpose of driving the drill bit 10 are not limiting: as an example, the motorized device 30 includes an electric motor whose output shaft is rotatably coupled about the drill axis X10 to the proximal end shank 14, as schematically illustrated in FIG. 2. Furthermore, in order to move the drill bit 10 in space, in particular along the direction of movement F1 when advancing the drill bit 10 in the pedicle P, the surgical treatment system 1 comprises a robot 40 that is shown only schematically in FIG. 2. This robot 40 consists of a robotic arm terminating in an end effector 41, for example, which is capable of being fixedly attached to the motorized device 30. Regardless of the embodiment of the robot 40, this robot 40 is adapted to move the motorized device 30 spatially.

During surgery, the movement by the robot 40 of the motorized device 30, and hence of the drill bit 10, is controlled by an electronic unit 50 receiving its instructions from a surgeon. Of course, the movements operated by the robot 40 are referenced spatially to a reference frame known to the electronic unit 50 and in which the vertebra V is positioned. Thus, after the surgeon has decided on the location he wishes to give to the hole T in the pedicle P of the vertebra V, in particular on the basis of preoperative and/or intraoperative data relating to this pedicle P, the surgeon gives corresponding instructions to the electronic unit 50, which then controls the robot 40 to move the motorized device 30, and thus the drill bit 10 driven in rotation by this device, relative to the vertebra V, so that the drill bit is applied to the latter and progresses in the pedicle P following the direction of movement F1.

According to an advantageous optional arrangement, the movement of the motorized device 30 by the robot 40 can be corrected during the drilling step when it is observed that the direction of movement F1 deviates from the axis of the hole T being made, in other words when the direction of movement F1 tends to lose its parallelism with the bit axis X10. To this end, the electronic unit 50 is adapted, in particular programmed, to control the movement operated by the robot 40 as a function of one or more spatial force component(s) exerted by the drill bit 10 on the vertebra V during drilling of the hole T. In practice, this or these force component(s) are measured by a force sensor 60, which is integrated into the motorized device 30 and which is adapted, for example, to provide an electrical signal representative of the deformation of the drill bit 10 during the drilling of the hole T. By means of a predetermined processing of the force component(s) measured by the force sensor 60, the electronic unit 50 ensures a positional control of the robot 40, which is kept in force and which is provided to maintain the direction of movement F1 aligned with the drill axis X10 and thus with the axis of the hole T being made, during the drilling of this hole by the drill 10. The benefits of force control are thus retained, while limiting or even eliminating the problem of possible drilling instabilities, particularly those related to slight changes in the orientation of the drill bit 10, due to play, and/or related to variations in the characteristics of the drilling environment for example, these variations being due to slight movements of the patient or the inhomogeneity of the drilled bone material, for example: the modification of the forces exerted by the drill 10 on the vertebra V during the drilling of the hole T is indeed indicative of such instabilities.

According to a preferred implementation of this position control method, operated by the electronic unit 50, the latter is configured, in particular programmed, to analyze the force component(s) measured by the force sensor 60, and then to control the robot 40 based on the result of this analysis. Several possibilities can be envisaged for the content of the analysis implemented by the electronic unit 50: for example, the latter is configured to compare the or each force component(s) with a predetermined value, or to follow this or these component(s) over time in order to detect a temporal drift. The electronic unit 50 may thus be configured to control the robot 40 so as to keep the or each of the effort components constant, to within a predetermined margin, of the order of a few percent.

Once the hole T is made at the end of the drilling step, the surgical treatment of the vertebra V continues with a screwing step in which the pedicle screw 20 is screwed into this hole T. However, the surgical treatment may include an optional intermediate step between the drilling step and the screwing step, this intermediate step being intended to check the positioning of the hole T in the vertebra V. For this purpose, the treatment system 1 comprises an intraoperative control member 70, shown only schematically in dotted lines in FIG. 3. This intraoperative control member 70 comprises, or even consists of, a probe, such as a rod, capable of being introduced into the hole T, as illustrated in FIG. 3. Whatever its form, the intraoperative control member 70 allows the surgeon to check that the hole T drilled into the vertebra V by the drill 10 is positioned in the latter in a suitable manner, in particular in accordance with what the surgeon had foreseen by the control instructions he had given to the electronic unit 50. The control performed by the surgeon can be performed directly by palpation of the intraoperative control member 70, more precisely of the part of the latter emerging from the hole T. This control can also be performed by intraoperative radiography when the intraoperative control member 70 is radiopaque, for example metallic. The surgeon can thus easily ensure that the upcoming screwing of the pedicle screw 20 can be performed without danger for the patient.

Figure 3:
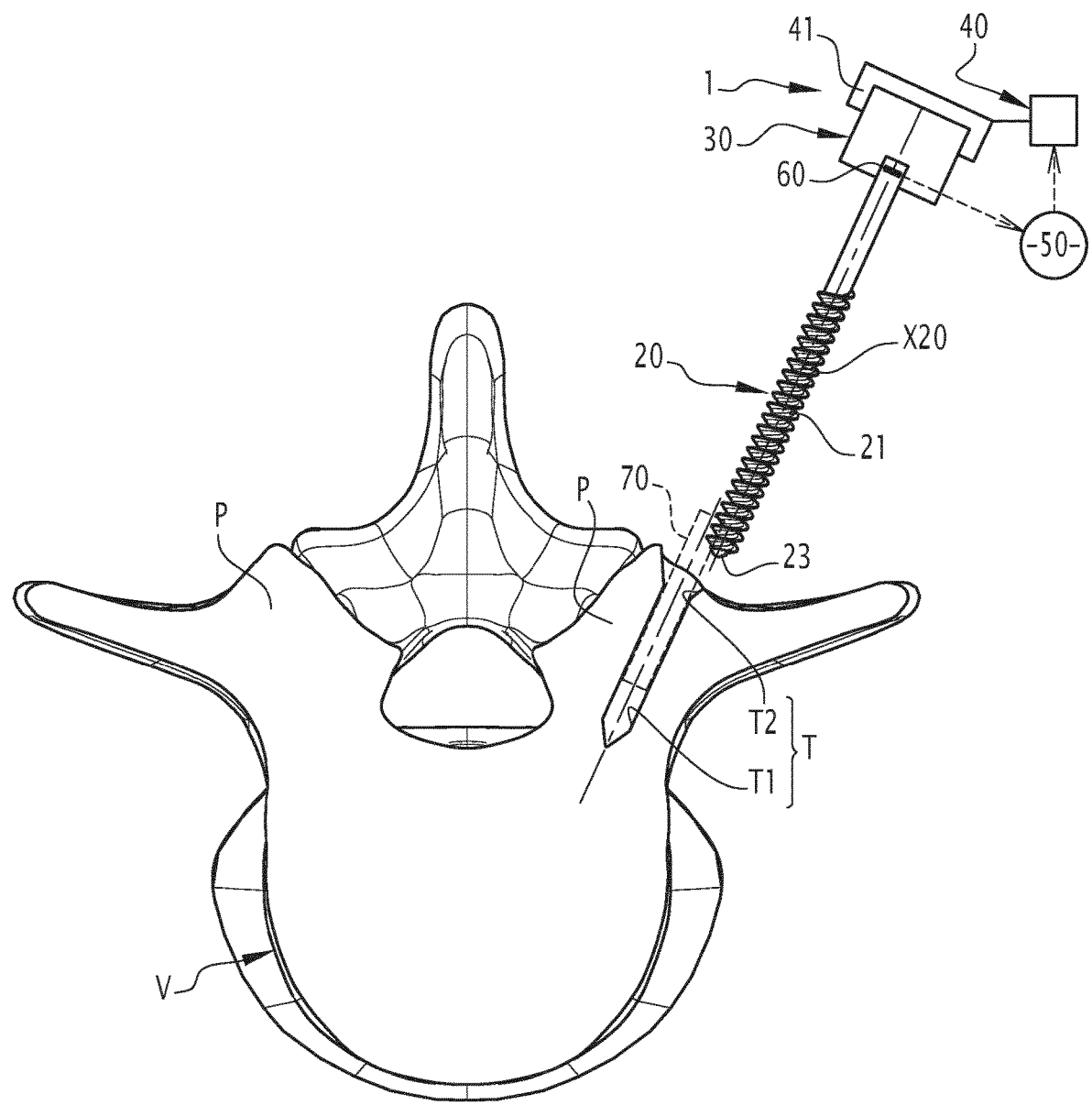

During the screwing step, the pedicle screw 20 is rotated about the screw axis X20 and is moved relative to the vertebra V so as to be inserted and advanced into the hole T, as illustrated in FIGS. 3 and 4. To this end, the motorized device 30 and the robot 40 are used in substantially the same way as in the drilling step, this time being applied to the pedicle screw 20: in particular, the motorized device 30 is connected to the head of the pedicle screw 20 for the purpose of driving the latter in rotation about the screw axis X20, and the movement of the threaded rod 21 in the hole T, operated by the robot 40, is carried out along a direction noted F2 in FIG. 4 and which extends parallel to the screw axis X20. Of course, the motorized device and/or the robot used in the screwing step may not be exactly the same as the motorized device 30 and/or the robot 40 used in the drilling step, but are similar in operation to the latter and are therefore shown and referenced in FIGS. 3 and 4 in the same way as in FIG. 2.

FIG. 3 illustrates when the pedicle screw 20 presents itself at the entrance to the hole T, before engaging the depth of the hole. In principle, the pedicle screw 20 is presented by the robot 40 at the entrance to the hole T so that the screw axis X20 is centered on the hole. However, for various reasons, including manufacturing clearances or inaccuracies and/or small patient movements, the screw axis X20 may not be strictly aligned with the axis of the hole T, as illustrated in FIG. 3. As soon as the distal end 23 of the threaded rod 21 begins to be inserted into the hole T, it contacts the funnel-shaped proximal end portion T2 of the hole T, so that this proximal end portion T2, as a ramp, brings the pedicle screw 20 into the axis of the hole T. In other words, the contact interaction between the funnel shape of the proximal end portion T2 of the hole T and the distal end 23 of the threaded rod 21 produces a centering effect of the pedicle screw 20 in the hole T. This centering effect is advantageously enhanced by the conical shape of the distal end 23. In any case, when the distal end 23 of the threaded rod 21 reaches and begins to progress into the distal end portion T1 of the hole T, the pedicle screw 20 is coaxial with the hole T.

The pedicle screw 20 then progresses within the hole T, its thread 22 engaging the wall of the distal end portion T1 of the hole T as the pedicle screw 20 is threaded in. The threaded rod 21 is thus inserted coaxially into the distal end portion T1 of the hole T, all the more precisely as the diameter of this distal end portion T1 is substantially equal to the diameter d21 of the threaded rod, measured at the base of the thread 22. If necessary, the pedicle screw 20 penetrates the vertebra V beyond the distal end of the distal end portion T1 of the hole T, penetrating without difficulty into the cancellous bone material of the vertebral body of the vertebra V.

Following considerations similar to those developed above in connection with the position control method, kept in force, which the electronic unit 50 implements during the drilling step, the movement by the robot 40 of the motorized device 30 and, thereby, of the pedicle screw 20 driven in rotation by the latter, is advantageously controlled as a function of one or more components of the forces exerted by the pedicle screw 20 on the vertebra V during the screwing in of the hole T. Thus, by processing these force component(s), measured by the sensor 60, the electronic unit 50 ensures a positional control of the robot 40, which is kept in force and which is provided to maintain the direction of movement F2 aligned with the screw axis X20 and thus with the axis of the hole T, during the screwing of the pedicle screw 20 into the hole. In practice, the explanations given above in connection with the drilling step apply to the screwing step mutatis mutandis.

In addition, various modifications and variants of the system and method of surgical treatment, described so far, are conceivable. For example, rather than the drill bit 10 and/or the pedicle screw 20 being rotated and moved spatially by the motorized device 30 and the robot 40, such drill bit and/or pedicle screw may be manually operated by the surgeon.

The invention claimed is:

1. A system for surgical treatment of the spine, comprising:
    a drill bit, that extends along a proximo-distal drill axis and that is suitable for drilling a hole in the pedicle of a vertebra of a patient when the drill bit is rotated on itself about the drill axis, this drill bit including, successively, along the drill axis:
    a distal end which is pointed and centered on the drill axis so as to be planted in bone material to be drilled of the pedicle of the vertebra,
    a cylindrical drill, centered on the drill axis and suitable for drilling the hole by cutting into and removing bone material from the pedicle of the vertebra so as to give a distal end portion of the hole a cylinder shape, and
    a milling cutter designed to cut the bone material from the pedicle of the vertebra so as to give a proximal end portion of the hole a funnel shape gradually widening from the distal end portion of the hole, and
    a pedicle screw that extends along a proximo-distal screw axis and that is designed to be screwed into the hole, by being rotated on itself about the screw axis, after the drill bit has drilled the hole in the pedicle of the vertebra and has been removed from this hole,
    wherein the pedicle screw includes a threaded rod, which comprises a distal end constituting a distal end of the pedicle screw, and which has a cylindrical shape, which is centered on the screw axis and whose nominal diameter is greater than a diameter of the drill, and
    wherein a helical drilling structure extends along the cylindrical drill and the milling cutter.

2. The system according to claim 1, wherein the milling cutter has a conical shape that is centered on the drill axis and diverges proximally from the drill.

3. The system according to claim 1, wherein the drill axis the drill is provided with helical grooves with a cutting edge, the helical grooves wind around the drill axis along the drill.

4. The system according to claim 1, wherein the diameter of the drill bit is substantially equal to the diameter of the threaded rod, measured at the base of the thread of the threaded rod.

5. The system according to claim 1, wherein the distal end of the threaded rod has a substantially conical shape, which is centered on the screw axis and diverges in the proximal direction.

6. The system according to claim 1, wherein the system further comprises an intraoperative control member, which is adapted to be introduced into the hole, after the drill bit has drilled the hole in the pedicle of the vertebra and has been removed from this hole and before the pedicle screw is screwed into the hole, so as to control the positioning of the hole in the vertebra.

7. The system according to claim 1, wherein the system further comprises:
    a motorized device adapted to rotate the drill bit about the drill axis or to rotate the pedicle screw about the screw axis, and
    a robot adapted to spatially move the motorized device.

8. The system according to claim 7, wherein the motorized device is equipped with a force sensor configured to measure at least one component of the forces exerted on the vertebra by the drill bit when drilling the hole or by the pedicle screw when screwing into the hole, and wherein the system further comprises an electronic unit adapted to control the movement of the motorized device by the robot as a function of said at least one component measured by the force sensor.

9. The system according to claim 8, wherein the electronic unit is configured both to analyze said at least one component measured by the force sensor and to control the movement of the motorized device by the robot from the result of the analysis of said at least one component.

10. The system according to claim 8, wherein the electronic unit is configured to control the movement of the motorized device by the robot so as to keep substantially constant the at least one component measured by the force sensor.

11. A method for drilling a vertebra of a patient via a system for surgical treatment, comprising:
    a drill bit, that extends along a proximo-distal drill axis and that is suitable for drilling a hole in the pedicle of a vertebra of a patient when the drill bit is rotated on itself about the drill axis, this drill bit including, successively, along the drill axis:
    a distal end which is pointed and centered on the drill axis so as to be planted in bone material to be drilled of the pedicle of the vertebra,
    a cylindrical drill, centered on the drill axis and suitable for drilling the hole by cutting into and removing bone material from the pedicle of the vertebra so as to give a distal end portion of the hole a cylinder shape, and
    a milling cutter designed to cut the bone material from the pedicle of the vertebra so as to give a proximal end portion of the hole a funnel shape gradually widening from the distal end portion of the hole, and a pedicle screw that extends along a proximo-distal screw axis and that is designed to be screwed into the hole, by being rotated on itself about the screw axis, after the drill bit has drilled the hole in the pedicle of the vertebra and has been removed from this hole, wherein the pedicle screw includes a threaded rod, which comprises a distal end constituting a distal end of the pedicle screw, and which has a cylindrical shape, which is centered on the screw axis and whose nominal diameter is greater than a diameter of the drill, and wherein a helical drilling structure extends along the cylindrical drill and the milling cutter;

the method comprising the steps of:

rotating the drill bit about the drill axis and moving the drill bit spatially by a robot, so as to drill the hole in the pedicle of the vertebra, measuring at least one component of the forces exerted by the drill bit on the vertebra during drilling of the hole, and controlling the movement of the drill bit by the robot as a function of said at least one component.

12. The method according to claim 11, wherein the movement of the drill bit by the robot is controlled based on an analysis of said at least one component, including by comparing said at least one component to a predetermined value or by time tracking said at least one component.

13. The method according to claim 11, wherein the movement of the drill bit by the robot is controlled to keep the at least one component substantially constant.

14. The method according to claim 11, wherein said at least one component is measured by a force sensor integrated with a motorized device that is adapted to rotate the drill bit about the drill axis and to be moved spatially by the robot.

15. A method for screwing into a vertebra of a patient via a system for surgical treatment, comprising:

a drill bit, that extends along a proximo-distal drill axis and that is suitable for drilling a hole in the pedicle of a vertebra of a patient when the drill bit is rotated on itself about the drill axis, this drill bit including, successively, along the drill axis:

a distal end which is pointed and centered on the drill axis so as to be planted in bone material to be drilled of the pedicle of the vertebra, a cylindrical drill, centered on the drill axis and suitable for drilling the hole by cutting into and removing bone material from the pedicle of the vertebra so as to give a distal end portion of the hole a cylinder shape, and a milling cutter designed to cut the bone material from the pedicle of the vertebra so as to give a proximal end portion of the hole a funnel shape gradually widening from the distal end portion of the hole, and a pedicle screw that extends along a proximo-distal screw axis and that is designed to be screwed into the hole, by being rotated on itself about the screw axis, after the drill bit has drilled the hole in the pedicle of the vertebra and has been removed from this hole, wherein the pedicle screw includes a threaded rod, which comprises a distal end constituting a distal end of the pedicle screw, and which has a cylindrical shape, which is centered on the screw axis and whose nominal diameter is greater than a diameter of the drill, and wherein a helical drilling structure extends along the cylindrical drill and the milling cutter;

the method comprising the steps of:

rotating the pedicle screw about the screw axis and moving the pedicle screw spatially by a robot, so as to screw the pedicle screw into the pedicle of the vertebra, measuring at least one component of the forces exerted by the pedicle screw on the vertebra during screwing of the pedicle screw, and controlling the movement of the pedicle screw by the robot as a function of said at least one component.

16. The method according to claim 15, wherein the movement of the pedicle screw by the robot is controlled based on an analysis of the at least one component, including by comparing the at least one component to a predetermined value or by time tracking the at least one component.

17. The method according to claim 15, wherein the movement of the pedicle screw by the robot is controlled to keep the at least one component substantially constant.

18. The method according to claim 15, wherein the at least one component is measured by a force sensor integrated with a motorized device that is adapted to rotate the pedicle screw about the screw axis and to be moved spatially by the robot.

* * * * *

UNITED STATES PATENT AND TRADEMARK OFFICE
CERTIFICATE OF CORRECTION

PATENT NO. : 12,089,857 B2
APPLICATION NO. : 17/430108
DATED : September 17, 2024
INVENTOR(S) : Romain Buttin et al.

Page 1 of 1

It is certified that error appears in the above-identified patent and that said Letters Patent is hereby corrected as shown below:

On the Title Page

Item (73) should read as follows:
--(73) Assignee: S.M.A.I.O. Saint-Priest, FR--

Signed and Sealed this
Tenth Day of June, 2025

Coke Morgan Stewart
*Acting Director of the United States Patent and Trademark Office*